United States Patent
Doerband et al.

(10) Patent No.: US 9,250,062 B2
(45) Date of Patent: Feb. 2, 2016

(54) DEVICES FOR DETERMINING LAYER THICKNESS AND/OR CONTAMINATION LEVEL OF A BELT

(71) Applicant: Carl Zeiss SMT GmbH, Oberkochen (DE)

(72) Inventors: Bernd Doerband, Aalen (DE); Ralf Lindner, Heidenheim (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 14/196,757

(22) Filed: Mar. 4, 2014

(65) Prior Publication Data

US 2014/0185060 A1 Jul. 3, 2014

Related U.S. Application Data

(63) Continuation of application No. PCT/EP2012/065162, filed on Aug. 2, 2012.

(30) Foreign Application Priority Data

Sep. 15, 2011 (DE) .......................... 10 2011 082 793

(51) Int. Cl.
*G01B 11/28* (2006.01)
*G01B 11/06* (2006.01)
*G01N 21/94* (2006.01)
*G01N 21/89* (2006.01)

(52) U.S. Cl.
CPC ................ *G01B 11/06* (2013.01); *G01N 21/89* (2013.01); *G01N 21/94* (2013.01); *G01N 2021/8908* (2013.01)

(58) Field of Classification Search
CPC .......... G01B 11/0625; G01B 11/0683; G01B 11/06; B24B 37/013; B24B 49/12
USPC ....................................... 356/630
See application file for complete search history.

(56) References Cited

U.S. PATENT DOCUMENTS

| 4,775,238 A | 10/1988 | Weber |
| 4,826,321 A * | 5/1989 | Coates et al. ................. 356/492 |

(Continued)

FOREIGN PATENT DOCUMENTS

| CN | 101466997 | 6/2009 |
| DE | 35 34 019 C2 | 5/1989 |

(Continued)

OTHER PUBLICATIONS

The International Preliminary Report on Patentability for corresponding PCT Appl No. PCT/EP2012/065162, dated Mar. 18, 2014.

(Continued)

*Primary Examiner* — Tarifur Chowdhury
*Assistant Examiner* — Md Rahman
(74) *Attorney, Agent, or Firm* — Fish & Richardson P.C.

(57) ABSTRACT

The invention relates to an apparatus for determining a layer thickness on a tape moved along a feed direction, comprising: a movement unit for moving the tape along the feed direction, a light generating unit for generating illumination radiation, a beam shaping unit disposed downstream of the light generating unit for shaping at least one strip-shaped illumination beam for linear illumination of the tape transversely with respect to the feed direction, a detector unit for detecting illumination radiation reflected and/or transmitted at the tape, and an evaluation device for determining the layer thickness on the basis of the detected illumination radiation. The apparatus can also be used for determining a degree of contamination of a surface of the tape, the surface being contaminated by particles, by detecting illumination radiation scattered at the tape.

20 Claims, 4 Drawing Sheets

(56) References Cited

U.S. PATENT DOCUMENTS

| | | | |
|---|---|---|---|
| 5,416,594 A * | 5/1995 | Gross et al. | 356/237.5 |
| 5,636,029 A * | 6/1997 | Zimmerman et al. | 356/626 |
| 5,696,389 A * | 12/1997 | Ishikawa et al. | 257/99 |
| 2003/0150272 A1 | 8/2003 | Janik | |
| 2005/0232570 A1 * | 10/2005 | Ide | 385/140 |
| 2008/0308244 A1 * | 12/2008 | Natori | 162/198 |
| 2009/0303468 A1 | 12/2009 | Itoh et al. | |
| 2010/0091618 A1 * | 4/2010 | Schabes et al. | 369/13.02 |
| 2014/0085393 A1 * | 3/2014 | Plotkin et al. | 347/118 |

FOREIGN PATENT DOCUMENTS

| | | |
|---|---|---|
| DE | 39 26 349 | 2/1991 |
| DE | 10 2006 044 307 | 9/2008 |
| EP | 1 041 379 A2 | 10/2000 |
| WO | WO 2012/042022 | 4/2012 |

OTHER PUBLICATIONS

German Office Action, with translation thereof, for corresponding DE Appl No. 10 2011 082 793.5, dated Jun. 20, 2012.

Thomas Riedl et al., "Thin Film Encapsulation of Top-Emitting OLEDs using Atomic Layer Deposition," Solid-State and Organic Lighting, OSA Technical Digest (CD) (Optical Society of America), paper SOWB5, 2010.

J. Meyer et al., "$Al_2O_3$ / $ZrO_2$ Nanolaminates as Ultra-high Gas Diffusion Barriers—a Strategy for Reliable Encapsulation of Organic Electronics," Adv. Mater. 18, 1845 (2009).

Peter van de Weijer and Ton von Mol, "White Paper on the Characterization of Thin-film Barrier Layer for Protection of Organic Light-Emitting Diodes", Sep. 10, 2009, 17 pages, retrievable on the Internet at "www.fast2light.org".

Masaru Nagai, "Impact of Particulate Contaminants on the Current Leakage Defect in OLED Devices", J. Electrochemical Soc. 154 (12) J387-J392 (2007).

Bawolek et al., "Light Scattering by Sub-half Micron Spherical Particles on Silicon and Oxidized Silicon Surfaces", Proc., ICCCS 485 (1992).

The International Search Report for corresponding PCT Appl No. PCT/EP2012/065162, dated Oct. 23, 2012.

Chinese Office Action with English translation thereof for corresponding CN Appl No. 201280055121.5, 21 pages, dated Jun. 18, 2015.

* cited by examiner

DEVICES FOR DETERMINING LAYER THICKNESS AND/OR CONTAMINATION LEVEL OF A BELT

REFERENCE TO RELATED APPLICATIONS

The present application is a continuation of, and claims benefit under 35 USC 120 to, international application PCT/EP2012/065162, filed Aug. 2, 2012, which claims benefit under 35 USC 119 of German Application No. 10 2011 082 793.5, filed Sep. 15, 2011. The entire disclosure of these applications is incorporated by reference herein.

BACKGROUND OF THE INVENTION

The invention relates to apparatuses for determining layer thicknesses on a tape and/or for determining a degree of contamination of a surface of a tape, the surface being contaminated by particles.

The tape or the tape-shaped body can have a plurality of layers and can be used e.g. in semiconductor fabrication for producing components appertaining to organic electronics, e.g. organic LEDs, or solar cells. In these applications, the tape is typically designed to be very thin or film-like, that is to say that the tape has a thickness which is typically in the micrometers range.

Components appertaining to organic electronics which can be fabricated from a tape-shaped substrate, for example, are sensitive to water and oxygen, inter alia, for which reason it is necessary to encapsulate these components relative to the environment. Such an encapsulation could be effected by glass or with the aid of metal hoods. However, such an encapsulation generally cannot be used for flexible, film-like and/or printed electronic components on account of its stiffness.

In order to encapsulate flexible components appertaining to organic electronics which are produced from tape-shaped substrates with a plurality of layers, it is possible to use, on both sides of the components, thin barrier layers (e.g. multilayers composed of $Al_2O_3$ and/or $ZrO_2$) having a sufficiently low water vapor transmission rate (WVTR), cf. the article "$Al_2O_3/ZrO_2$ Nanolaminates as Ultra-high Gas Diffusion Barriers—a Strategy for Reliable Encapsulation of Organic Electronics", by J. Meyer et al. Adv. Mater. 18, 1845 (2009) or the article "Thin Film Encapsulation of Top-Emitting OLEDs using Atomic Layer Deposition" by Thomas Riedl et al., in Solid-State and Organic Lighting, OSA Technical Digest (CD) (Optical Society of America, 2010), paper SOWB5.

It is problematic for the production of organic electronic components, however, if there are particles present on the surface to which the barrier layer is intended to be applied, since the particles firstly can form microchannels which enable water and/or oxygen from the environment to pass through the barrier layer, and secondly can lead to electrical short circuits between the electrodes of the organic components. Water and oxygen are critical in particular in the production of organic LEDs (OLEDs), since they can lead to oxidation of the cathode, which in OLEDs generally consist of a base metal (e.g. aluminum), with the result that current can no longer flow locally (cf. "White Paper on the Characterization of Thin-film Barrier Layer for Protection of Organic Light-Emitting Diodes" by Peter van de Weijer, Ton von Mol, 10 Sep. 2009, retrievable on the Internet at "www.fast2light.org"). This can lead to black points on the surface emitters and possibly to failure of the OLED.

Organic electronic components are generally processed either in clean rooms (e.g. having permissible particle sizes of a maximum of 0.5 µm), in a vacuum or under a protective gas atmosphere. In this case, care should be taken to ensure that the substrates or surfaces used are free of particles. In particular, no particles which penetrate the barrier layers and the electrodes, in particular the cathode (in the case of an OLED), should be present in the region of an electronic component. Smaller particles which are still covered by the barrier layer or which are present only in the inner layers of the component are less critical, by contrast. The minimum critical particle size is therefore the sum of the smallest occurring layer thicknesses of barrier layer and electrode, i.e. typically in the region of approximately 0.15 µm.

During the process for producing OLEDs, the largest particles are produced when the anode (generally composed of indium tin oxide (ITO)) is applied to the carrier material by a sputtering process, wherein the particle sizes in this process step can be approximately 5 µm, cf. "Impact of Particulate Contaminants on the Current Leakage Defect in OLED Devices" by Masaru Nagai, J. Electrochemical Soc. 154, J387 (2007). However, these particles can readily be removed by cleaning Residual ITO particles may be critical with regard to short circuits, but generally not for the diffusion of water on the anode side, since there the barrier layer is applied before the ITO layer and is therefore not penetrated by particles in that they do not arise until as a result of the ITO sputtering. Smaller particles that do not penetrate the conductive layers (ITO anode, shunting lines, conductive polymer layers) are comparatively noncritical, by contrast.

It is known to observe the surfaces of substrates with the aid of cameras. However, the resolution (>10 µm) of the cameras is generally not sufficient for identifying or detecting small particle sizes of less than 10 µm. Other solutions having a high resolution use a point-type measurement (cf. "Light Scattering by Sub-half Micron Spherical Particles on Silicon and Oxidized Silicon Surfaces", Bawolek et al. Proc., ICCCS 485 (1992)) and are therefore typically too slow to examine the entire surface (in a scanning manner) in situ during a production process or are generally unsuitable for process monitoring (e.g. solutions with electron microscopes).

Besides determining the degree of contamination of the surface of a tape-shaped body by particles or determining the particle density on the surface, for the processing of the tape it is also advantageous to determine the thickness or the refractive index of the tape or of individual layers of the tape with a high spatial resolution. Typically, the coarse layer construction of the tape is already known in this case. The measurement accuracy when determining the layer thickness (in the case of average thicknesses of the order of magnitude of approximately 100 nm) should be as high as possible (typically <2 nm), however, and the measurement should be able to be carried out at high speed and with a spatial resolution (grid) of an order of magnitude of approximately 100 µm, which cannot be accomplished by conventional apparatuses for thickness measurement at the present time.

Object of the Invention

It is an object of the invention to provide an apparatus or apparatuses for determining layer thicknesses on a tape and/or for determining a degree of contamination of a surface of a tape, the surface being contaminated by particles, which in particular can also be used in production processes directly (in situ or inline).

SUBJECT MATTER OF THE INVENTION

This object is achieved, in accordance with a first aspect, via an apparatus for determining a degree of contamination of a surface of a tape moved along a feed direction, the surface being contaminated by particles, comprising: a light generating unit for generating illumination radiation, a beam shaping unit disposed downstream of the light generating unit and serving for shaping at least one strip-shaped illumination beam for illuminating the tape-shaped sample transversely with respect to the feed direction, a detector unit for detecting illumination radiation scattered at the tape-shaped sample, and an evaluation device for determining the degree of contamination of the surface using the detected illumination radiation.

The invention proposes providing a (stationary) apparatus for monitoring in situ the degree of contamination or for detecting particles on the surface of a tape, while the tape is moved relative to the apparatus along a feed direction. For this purpose, a linear illumination is used, which typically extends over the entire width of the tape to be inspected, in order to determine the degree of contamination over the entire width of the tape. In this case, the tape can be moved in the feed direction via driven rollers, for example. The linear illumination in this case enables a parallel measurement at a plurality of measurement locations transversely with respect to the feed direction.

Within the meaning of this application, the expression "transversely with respect to the feed direction" is understood to mean an orientation of the strip-shaped illumination beam which runs at an angle (different from 0°) with respect to the feed direction, wherein the angle is typically 90° or else can deviate from 90° (e.g. by +/−30°). A "linear illumination" is understood to mean an illumination which generates on the tape a line whose length substantially corresponds to the width of the tape and whose line width is in the micrometers or sub-micrometers range and, for example, does not exceed a line width of approximately 50 µm or of approximately 5 µm.

The movement of the sample in the feed direction in combination with the linear illumination enables the sample to be inspected or monitored rapidly with regard to contaminating particles. The use of a stray light measurement for detecting particles makes it possible in this case to measure the degree of contamination even for particles having small particle sizes of less than approximately 10 µm, e.g. of 6 µm or less. In this case, one or a plurality of apparatuses for monitoring the degree of contamination can be mounted at different locations in a production installation for an organic component, for example an OLED. The apparatuses make it possible to ensure that the surface is sufficiently free of particles for a subsequent production step, e.g. a subsequent coating step.

In one embodiment, the beam shaping unit is designed for linear illumination of the tape with a line width that is variable in the feed direction. Inter alia, the (average) particle size of the particles which can be detected with the aid of the stray light measurement depends on the line width of the strip-shaped illumination beam. In this regard, particles in the size range of approximately 0.1 µm up to a size range of approximately 6 µm can be detected separately depending on the line width e.g. in a range of between approximately 0.5 µm and 10 µm.

In one embodiment, the beam shaping unit has at least one optical element having an adjustable focal length. The optical element can be, for example, a lens element or a mirror that can be varied in terms of shape or geometry, such that the focal length thereof is adjustable. It goes without saying that, for the purpose of focusing, a zoom lens having a variable focal length can also be provided in order to vary the line width of the strip-shaped illumination beam on the surface.

In a further embodiment, the beam shaping unit has at least one telescope arrangement for the beam expansion of the illumination radiation in the feed direction. Such a telescope arrangement has two optical elements arranged at the distance of their focal lengths from one another. The optical elements can be reflective or refractive optical units. In one advantageous development, at least one of the optical elements of the telescope arrangement has an adjustable focal length in order to set the line width of the strip-shaped illumination beam on the tape. The expanded illumination beam typically has an aspect ratio of less than 1:50, generally of less than 1:10 (width:length). It is reduced in terms of its line width via a focusing unit typically at least by a factor of 100, if appropriate by a factor of more than 10 000, e.g. by a factor of approximately 85 000.

In one embodiment, the evaluation device is designed for detecting the exceeding of a limit value of the degree of contamination and/or of a limit value of the change in the degree of contamination of the surface. The degree of contamination with particles is understood hereinafter to mean, in particular, the particle density, i.e. the number of particles per area element on the surface of the tape. If particles are situated on the tape or on the surface, then they lead to a local increase in the stray light intensity, on the basis of which the particle density and thus the degree of contamination of the surface can be deduced. On account of the linear illumination or detection, stray light from different particles may possibly be superimposed on one another. Therefore, it is generally not possible to specify an exact particle density and simultaneously a size distribution of the particles. However, the evaluation unit can instead assign the integral stray light intensity to a specimen particle distribution of uniform particle size which was measured beforehand for calibration for a respective type of tape or substrate and which is stored in the evaluation unit. Changes in this assigned particle density and, in particular, fluctuations of this assigned particle density can be detected and, e.g. in the event of a limit value being exceeded, an alarm can be issued, such that measures for reducing the particle density can be initiated by machine or by an operator.

In a further embodiment, the evaluation device is designed for determining a degree of contamination of the surface on a plurality of tape sections each extending in the feed direction, that is to say that the particle density is determined integrally for respective tape sections typically of identical length, wherein the results can be stored in a storage device. If the tape is moved at a constant velocity, the stored results can be assigned to the respective tape sections in a particularly simple manner (via a time measurement). If the velocity of the tape varies, it is advantageous to provide markings on the tape, which markings can be detected via a camera, for example, such that an unambiguous assignment of detected particle densities to tape sections is possible.

On those tape sections on which an excessively high particle density was determined, (if appropriate renewed) cleaning can be carried out via a cleaning device disposed downstream of the apparatus for particle detection in the feed direction. Alternatively, it is also possible for tape sections in which the limit value of the degree of contamination was overshot to be excluded from further processing. It goes without saying that, in order to limit the stored volume of data, if appropriate only conspicuous results should be stored, e.g. only particle densities of sections which are above the limit value.

In a further embodiment, the apparatus comprises a reference detector for determining the intensity of the illumination radiation generated by the light generating unit. With the aid of the signal recorded by the reference detector, fluctuations of the intensity of the illumination radiation generated by the light generating unit during the measurement can be detected and therefore eliminated by a comparison being made with the stray light intensity detected by the detector unit. This detected stray light intensity depends on the surface roughness and on the correlation length of the surface. The stray light intensity is all the greater, the greater the roughness and the shorter the correlation length of the surface. Stray light intensities of typical surface roughnesses and/or correlation lengths can be stored for diverse angles of incidence and detection angles in the evaluation unit and can be used as a reference for the stray light intensity of the particles, in order to determine the proportion of the particles with respect to the total stray light intensity (particles+surface). Ideally, it is possible to completely eliminate the contribution of the surface for the determination of the particle density, i.e. only intensity noise (on the zero line) is measured on a particle-free surface.

A further aspect of the invention relates to an apparatus for determining a layer thickness on a tape moved along a feed direction, comprising: a movement unit for moving the tape along the feed direction, a light generating unit for generating illumination radiation, a beam shaping unit disposed downstream of the light generating unit for shaping at least one strip-shaped illumination beam for linear illumination of the tape transversely with respect to the feed direction, a detector unit for detecting illumination radiation reflected and/or transmitted at the tape, and an evaluation device for determining the layer thickness using the detected illumination radiation. In order to determine the layer thickness of individual layers of the tape or, if appropriate, of the entire tape, instead of the radiation scattered at the tape, illumination radiation reflected and/or transmitted by the tape is detected, i.e. the angle of incidence of the illumination radiation on the tape corresponds to the detection angle. By virtue of the linear, parallelized illumination and detection, it is possible in this case to perform a rapid and simultaneously precise thickness determination which can be used, in particular, in situ in processes for producing electronic components. In this case, the reflection and/or the transmission of the tape can be determined via a light generating device which generates illumination radiation having a broadband spectrum, or with the aid of illumination radiation at one or a plurality of discrete wavelengths.

In one embodiment, the apparatus additionally comprises a polarization filter device for setting the polarization of the illumination radiation. In this case, the direction of polarization can be set via suitable filters e.g. perpendicular or parallel to the plane of incidence of the illumination radiation on the tape (s- or p-polarization).

In one development, the polarization filter device can switch over between two mutually orthogonal polarization states (e.g. s- and p-polarization). This is advantageous since the reflectivity or the transmission of the illumination radiation is influenced not only by the wavelength but also by the polarization of the incident illumination radiation (cf. Fresnel equations). The additional degree of freedom of polarization makes it possible to increase the measurement accuracy and also to increase the measurement range in which the thickness measurement can be carried out with high precision.

In one embodiment, the movement unit is designed for moving the tape at a velocity of at least 1 m/min, preferably of at least 10 m/min, in particular of 50 m/min or more. Such velocities require a correspondingly high speed when recording measurement data (e.g. of 0.12 ms at 50 m/min), which can be achieved by the linear illumination (and the linear detection) since this enables the parallel detection of the layer thickness over the entire width of the tape.

A further aspect of the invention is realized in an apparatus for determining a degree of contamination of a surface contaminated by particles and/or a layer thickness on a tape moved along a feed direction, comprising: a light generating unit for generating illumination radiation, a beam shaping unit disposed downstream of the light generating unit for shaping at least one strip-shaped illumination beam and for linear illumination of the surface of the tape transversely with respect to the feed direction, a detector unit for detecting illumination radiation scattered, reflected and/or transmitted at the tape, and an evaluation device for determining the degree of contamination of the surface and/or the layer thickness using the detected illumination radiation. Advantageously, one and the same apparatus can be used to determine both the particle density on the surface of the tape and the thickness of the tape or of individual layers of the tape. In this case, the particle density and the thickness can be measured sequentially by the angle of incidence or the detection angle being varied, e.g. from a detection angle for detecting stray light to a detection angle for detecting (specularly) reflected illumination radiation.

It goes without saying that the detector unit in the apparatus can, if appropriate, also have two or more detectors in order to enable a parallel determination both of the particle density and of the layer thickness. In this case, one of the detectors is arranged e.g. at a detection angle corresponding to the angle of incidence, while a further detector is arranged at a detection angle that deviates from the angle of incidence, in order to detect the illumination radiation scattered at the tape.

It goes without saying that the additional features specified above in association with the respective apparatus for determining the degree of contamination or for layer thickness measurement can also be used in the combined apparatus. In particular, in this case, the line width of the linear illumination can be adapted since the line widths for determining the particle densities and for the layer thickness measurement possibly deviate from one another.

In one embodiment, the light generating unit has at least one light source for generating illumination radiation in a wavelength range of between 300 nm and 1000 nm. The use of illumination radiation in this wavelength range has proved to be advantageous for the present applications. The illumination radiation can be provided in a broadband fashion by the light source, i.e. over a wide spectral range of e.g. from 400 nm to 800 nm (white light spectrum, e.g. generated by a lamp).

In a further embodiment, the light generating unit has at least one light source for generating illumination radiation at a predefined wavelength. By way of example, lasers, laser diodes, LEDs or gas discharge lamps can serve as light sources that generate radiation at discrete wavelengths. For the stray light measurement, it is advantageous to use illumination radiation at a single predefined wavelength or in a limited wavelength range.

In one development, the light generating device has at least two light sources for generating illumination radiation having different wavelengths. For the layer thickness determination, in particular, it has proved to be advantageous to use two or more, in particular three, light sources, the wavelengths of which can be in the red, green and blue spectral range, for example, in order to increase the measurement accuracy and/or the measurement range.

In one embodiment, the detector device has at least one spectrally resolving (and typically also spatially resolving) detector for simultaneously detecting the illumination radiation at two or more different wavelengths. In this case, the detector can have, in particular, sensor elements which are sensitive to illumination radiation in the red, green and also blue spectral range or decompose white light into these three components. A simultaneous detection of the illumination radiation for all three wavelengths used can take place in this way.

In one embodiment, the detector device has at least one spatially resolving detector for the spatially resolved detection of the illumination radiation transversely with respect to the feed direction. The detector can have, for example, a plurality of sensors in a line in order to perform a one-dimensional, line-like detection of the illumination radiation. However, the detector can also have a plurality of sensors or sensor lines in a grid arrangement in order to be able to perform a two-dimensional, strip-shaped detection of the illumination radiation. In this case, the detector area has a normal direction corresponding to the detection angle of the detected illumination radiation. It is advantageous for precise layer thickness determination if the detector has a spatial resolution of at least 100 µm.

In one embodiment, an angle of incidence of the strip-shaped illumination beam on the surface of the tape and/or a (respective) detection angle for detecting illumination radiation reflected, transmitted and/or scattered at the tape are/is adjustable. In order to adjust the angle of incidence, the beam shaping unit can be displaced and/or pivoted if appropriate together with the light generating unit or the light source. For this purpose, provision can be made of movement units e.g. in the form of rotational and/or translational drives and/or motors in the apparatus. Accordingly, by pivoting and/or displacing one or a plurality of detectors of the detector unit, it is possible to adjust the orientation of the respective detector area relative to the tape and thus the detection angle.

When detecting particles, it is possible to adjust the angle of incidence and/or the detection angle in order to influence the local ratio of surface stray light to particle stray light, which is dependent on the respective surface constitution or on the type of material. In order to be able to reliably detect particle stray light, the angle of incidence and/or the detection angle should be chosen such that the ratio is greater than one. The detection angle should be chosen here in any case such that neither the specular reflection (angle of incidence=angle of reflection) nor the illumination radiation transmitted at the tape impinges on the detector. In the case also of the thickness measurement at the substrate, the angle of incidence and/or the detection angle can be chosen such that in the expected measurement range for the layer thickness the change in reflection depending on the layer thickness is particularly large.

Further features and advantages of the invention are evident from the following description of exemplary embodiments of the invention, with reference to the figures of the drawing, which show details essential to the invention, and from the claims. The individual features can be realized in each case individually by themselves or as a plurality in any desired combination in a variant of the invention.

DRAWING

Exemplary embodiments are illustrated in the schematic drawing and are explained in the following description. In the figures.

Figure 1:
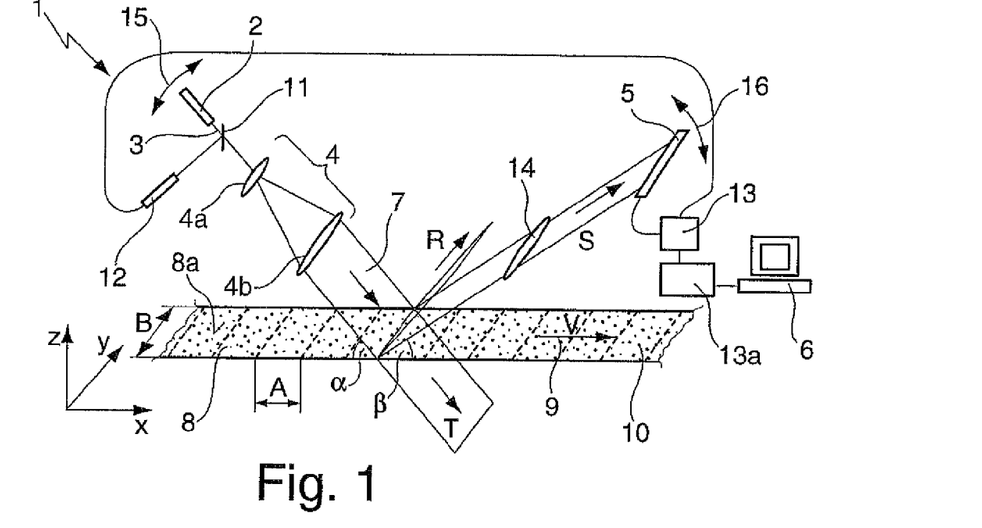
FIG. 1 shows a schematic illustration of an apparatus in which a stray light measurement is carried out for detecting particles on a surface of a tape moved along a feed direction.

FIG. 1 schematically shows an apparatus 1 comprising a light generating unit 2 having a single light source in the form of an He—Ne laser for generating illumination radiation 3, a beam shaping unit 4 disposed downstream in the beam path, and a detector unit 5, which is signal-connected to an evaluation device 6, e.g. in the form of a computer.

The beam shaping unit 4 serves for shaping a strip-shaped illumination beam 7 and for focusing the illumination beam 7 at an angle $\alpha$ of incidence on a tape 8, which, in the present example, is a substrate for producing organic LEDs (OLEDs). The beam shaping unit 4 has two parts, namely an expansion unit 4a for shaping the strip-shaped illumination beam 7 and a focusing unit 4b for focusing the strip-shaped illumination beam 7 on the tape 8 in order to obtain a linear illumination there.

The tape 8 is moved at a substantially constant velocity v along a feed direction X via a conventional movement device 9 indicated by an arrow (e.g. via driven rollers). The tape 8 can be unwound for example from a reel (not shown) or can be transported from a previous process station—e.g. for applying a coating—into the region of the apparatus 1. The velocity v of the tape 8 is typically of the order of magnitude of approximately 1 m/min to approximately 50 m/min.

In the present example, the detector unit 5 consists of a linear detector having a detector line running perpendicularly to the feed direction X of the tape 8 (i.e. in the Y-direction), i.e. parallel to the focal line formed by the strip-shaped illumination beam 7 on the tape 8. It goes without saying that the strip-shaped illumination beam 7 or the focal line need not necessarily be oriented perpendicularly to the feed direction X, although a perpendicular orientation has proved to be advantageous in practice.

The detector unit 5, resp., the normal to the detector area is oriented relative to the tape 8 at a detection angle $\beta$ with respect to the surface 8a of the tape 8. In the case of the apparatus 1 shown in FIG. 1, the detection angle $\beta$ ($\neq\alpha$) deviates from the angle $\alpha$ of incidence, such that only illumination radiation S scattered at the tape 8 and only an extremely small proportion of specularly reflected illumination radiation R and of transmitted illumination radiation T impinge on the detector unit 5.

In the example shown in FIG. 1, an individual (cw) laser 2 is used as a light source. It goes without saying that alternatively a (cw) laser diode can also be used, provided that the output power thereof suffices to illuminate the tape 8 sufficiently over the entire width thereof (in the Y-direction). Alternatively, it is also possible to use a plurality of light sources arranged in an offset manner in the Y-direction in a line, for example, in order to illuminate the tape over the entire width thereof, wherein a respective light source is assigned to a respective width range along the width direction (Y-direction) of the tape 8. When a plurality of light sources are used as the light generating unit, the power of an individual light source can turn out to be lower, with the result that such a solution is appropriate, in particular, for large widths B of the tape 8 of e.g. more than 1 to 2 meters.

The wavelength of the illumination radiation 3 for the stray light measurement should typically be between approximately 600 nm and 900 nm, wherein the polarization of the laser radiation can be chosen arbitrarily, but preferably runs perpendicularly to the plane of incidence (s-polarization). The He—Ne laser used as the light generating unit 2 in the present example has a wavelength of around approximately 635 nm with an output power of 2 watts and can be used e.g. for a tape 8 having a width B of approximately 30 cm. Alternatively, for illuminating a width B of 30 cm, it is also possible to use four laser diodes arranged in a line and having a power of in each case 500 mW.

It goes without saying that a (gas discharge) lamp, which advantageously has at least one spectral line having a wavelength in the spectral range of approximately 600 nm to 900 nm, can also be used as the light source. The illumination radiation generated by the lamp can be collimated with the aid of optical elements (e.g. lens elements or the like) before the strip-shaped illumination beam 7 is generated. If a light source having broadband emission (e.g. an incandescent lamp) is used, the spectrum of the illumination radiation should be restricted with the aid of filters to the wavelength range desired for the stray light measurement.

A small portion (generally <10%) of the intensity of the illumination radiation 3 generated by the light generating unit 2 is deflected via a beam splitter 11 and impinges on a reference detector 12. The beam splitter 11 can consist of a substrate which is coated on one side or on both sides or is uncoated. By way of example, a laser power measuring instrument or, if appropriate, a photodiode can serve as the reference detector 12. When measuring the laser power, care should be taken to ensure that the detector area is larger than the impinging beam cross section. If appropriate, it is necessary for this purpose to focus the coupled-out illumination radiation, which can be achieved e.g. via a convex lens element (not shown).

When using a light generating unit 2 having a plurality of light sources, it is possible to use a single reference detector 12 for all the light sources, or it is possible to provide two or more reference detectors which are assigned in each case to a plurality of light sources. In the case with the highest outlay, a dedicated reference detector is assigned to each light source. The intensity signal supplied by the reference detector 12 and a corresponding signal from the detector 5 are fed to an amplifier 13 and amplified there before being digitized in an A/D converter 13a and fed to the evaluation unit 6.

The evaluation unit 6 serves for determining the degree of contamination of the surface 8a, which is produced by particles 10 deposited there. In the present example, the degree of contamination is determined via the particle density on the surface 8a of the tape 8. In this case, the presence of particles 10 on the surface 8a leads to local increases in the stray light intensity, on the basis of which the particle density can be deduced. Stray light intensities of samples having a known particle distribution which are stored in the evaluation unit 6 can be used for calibration purposes. The contribution of the surface to the scattering can also be taken into account by virtue of the stray light intensities for typical surface roughnesses and correlation lengths being stored for diverse angles $\alpha$ of incidence and detection angles $\beta$. In this case, the angle $\alpha$ of incidence and the detection angle $\beta$ can be chosen, in particular, such that the ratio between illumination radiation S locally scattered at the surface 8a and illumination radiation S locally scattered at the particles 10 becomes as high as possible, but at least greater than one.

Since stray light for a plurality of particles 10 possibly having different particle sizes is superimposed on one another on account of the line- or stripwise detection, it is generally problematic to determine the particle density and a precise size distribution of the particles 10 simultaneously. Therefore, the evaluation unit 6 assigns the integral particle stray light intensity to a particle distribution having a uniform particle size, on the basis of which the exceeding of a limit value of the change in the particle density and/or the exceeding of a limit value of the particle density during the movement of the tape 8 can be determined.

In the example shown in FIG. 1, such a determination is performed for tape sections A which extend in each case over a length of approximately 10 cm in the feed direction X and for which the particle density or the stray light intensity is determined integrally in each case. If the tape 8 is moved at a constant velocity v, the stored results can be assigned to the respective tape sections A in a particularly simple manner (via a time measurement). If the velocity v of the tape 8 varies, it is advantageous to provide on the tape markings which can be detected e.g. via a camera (not shown), such that an unambiguous assignment of detected particle densities to tape sections A is possible.

At those tape sections A at which an excessively high density of particles 10 was determined, (renewed) cleaning can be carried out for example via a cleaning device situated downstream of the apparatus 1 in the feed direction X. Alternatively, it is also possible for tape sections A in which the limit value of the degree of contamination was exceeded to be excluded from further processing. It goes without saying that, in order to limit the stored volume of data, if appropriate, only conspicuous results should be stored, e.g. only particle densities of tape sections A which are above the limit value. A sudden change in the particle density, for example an abrupt rise in the particle density, can also be identified in the evaluation unit 6 and used to initiate an alarm, such that an operator can, if appropriate, track down the source of the particles and eliminate the latter.

Exemplary embodiments of the expansion unit 4a of the beam shaping unit 4 are described below with reference to FIG. 2 to FIG. 4. It is assumed here that the illumination radiation 3 emerging from the light generating unit 2 enters into the expansion unit 4a in a collimated fashion and parallel to the optical axis. It goes without saying that the light sources used (lasers, laser diodes or collimated lamp beams) have a greater or lesser divergence that is compensated for by optical units (not shown) via the focal lengths and spacings of the optical units used being correspondingly adapted. The optical units used for this purpose should be designed such that the illumination beams are not trimmed.

Figure 2:
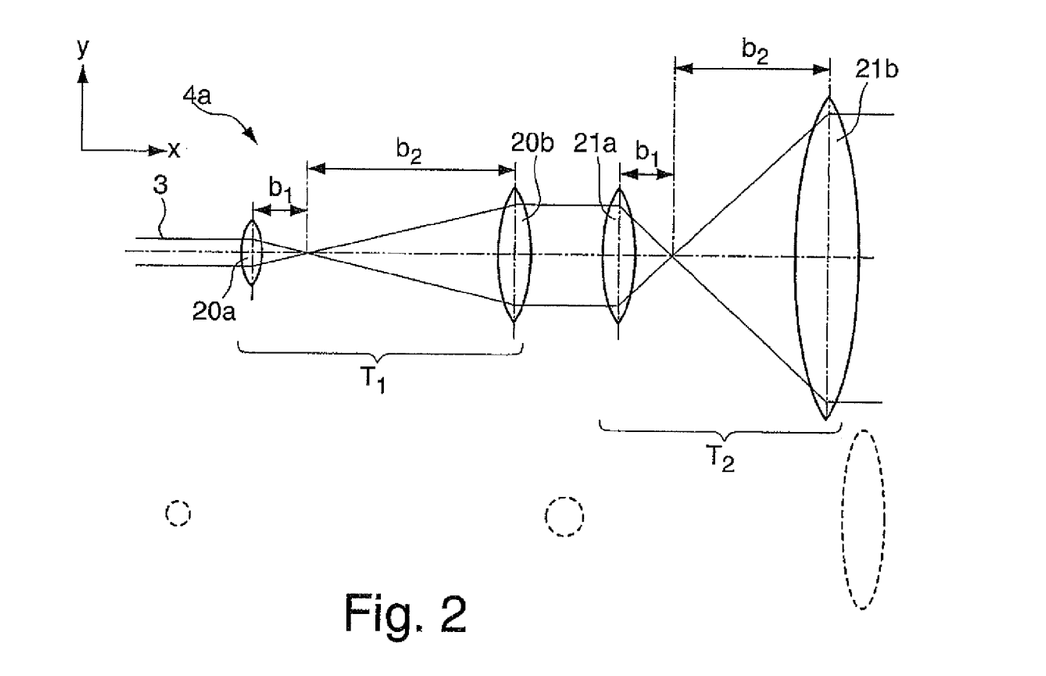
FIG. 2 shows a schematic illustration of one exemplary embodiment of a beam shaping unit having two beam telescopes for shaping a strip-shaped illumination beam for the apparatus from FIG. 1.

FIG. 2 shows an exemplary embodiment of the expansion unit 4a in a projection into the XY-plane. The expansion unit 4a has two telescope arrangements $T_1$, $T_2$ each having two lens elements 20a, 20b, 21a, 21b, in order to expand the round beam cross section of the illumination radiation 3, illustrated at the bottom left in FIG. 2. The first telescope $T_1$ has two spherical convex lens elements 20a, 20b, which are arranged at a distance corresponding to the sum of their focal lengths b1+b2. If the beam cross section is intended to be magnified e.g. by the factor eight (8×), the first spherical lens element 20a can have a focal length of 10 mm and the second spherical lens element 20b can have a focal length of 80 mm. It goes without saying that an eight-fold magnification can also be achieved if e.g. the first lens element 20a is replaced by a (spherical) concave lens element having a focal length of b1=−10 mm.

The second beam telescope $T_2$ consists of two cylindrical lens elements 21a, 21b, which further magnify the illumination radiation 3 perpendicularly to the plane of incidence (i.e. perpendicularly to the feed direction X) of the tape 8. In order to achieve for example an expansion by the factor 37.5 for the illumination radiation 3, a focal length b1 of 10 mm is used for the first cylindrical lens element 21a and a focal length b2 of 375 mm is used for the second cylindrical lens element 21b, such that an oval beam cross section is generated from the round beam cross section, the oval beam cross section being illustrated (not true to scale) at the bottom right in FIG. 2. It goes without saying that in this case, too, the first, convex cylindrical lens element 21a can be replaced by a concave cylindrical lens element having a focal length b1 of −10 mm, in order to achieve a beam expansion by the factor of 37.5.

Via the expansion unit 4a in FIG. 2, therefore, in the present example, illumination radiation 3 having a round beam cross section and a diameter of 1 mm can be expanded at the first telescope $T_1$ into a round beam cross section having a diameter of 8 mm and at the second telescope $T_2$ into an oval beam cross section having a length of 300 mm and a width of 8 mm, which is focused as a strip-shaped illumination beam 7 on the tape 8 via the focusing unit 4b and in this case is reduced in terms of its extent in the feed direction X (see below).

Figure 3:
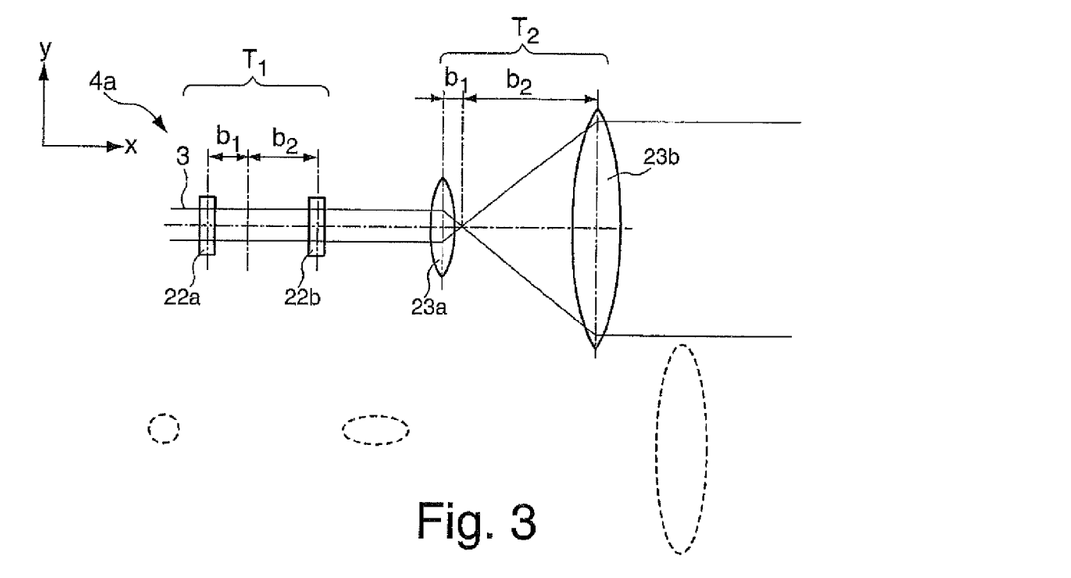
FIG. 3 shows a further exemplary embodiment of a beam shaping unit having two beam telescopes, each having two cylindrical lenses.

FIG. 3 shows a further exemplary embodiment of the expansion unit 4a, wherein both telescope arrangements $T_1$, $T_2$ consist of cylindrical lens elements 22a, 22b, 23a, 23b. In this case, the first telescope arrangement $T_1$ expands the illumination radiation 3 parallel to the plane of incidence on the tape 8, and the second telescope arrangement $T_2$ expands the illumination radiation 3 perpendicularly thereto (in the Y-direction), with the result that the oval beam cross section illustrated at the bottom right in FIG. 3 arises. If this beam cross section is intended to be identical to the example shown in FIG. 2, the focal lengths of the first telescope arrangement $T_1$ of the expansion unit 4a from FIG. 2 can be adopted, while for the second telescope arrangement $T_2$ the focal length of the first cylindrical lens element 23a is b1=10 mm (or −10 mm) and the focal length b2 of the second cylindrical lens element 23b is b2=3000 mm.

Figure 4:
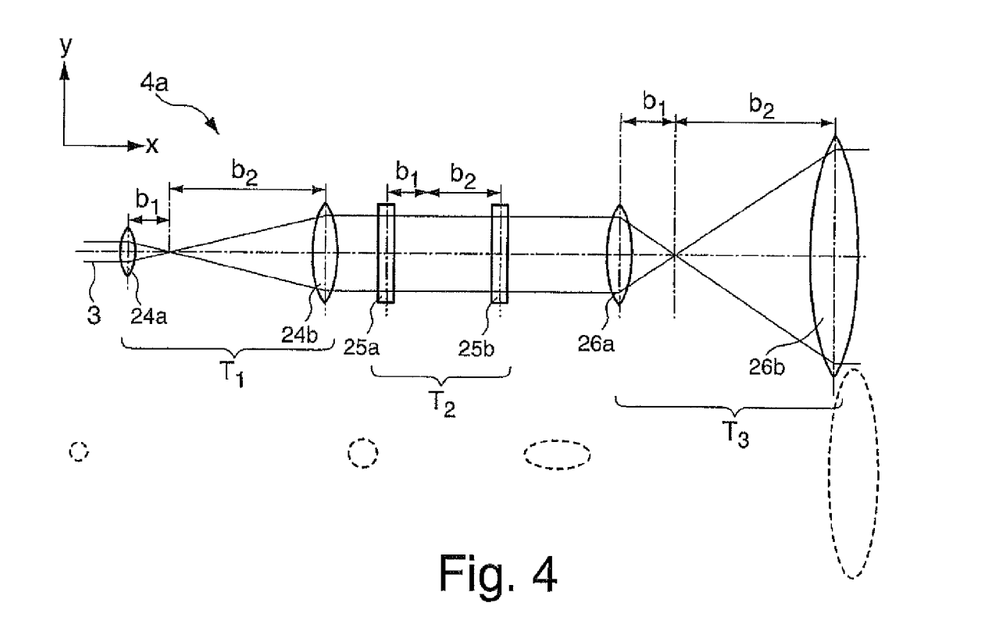
FIG. 4 shows one exemplary embodiment of the beam shaping unit having three beam telescopes.

In one exemplary embodiment of the expansion unit 4a, as shown in FIG. 4, three telescope arrangements $T_1$, $T_2$, $T_3$ each having two lens elements 24a, 24b, 25a, 25b, 26a, 26b are used for beam expansion. The first telescope arrangement $T_1$ has two spherical lens elements 24a, 24b and can have focal lengths of b1=+10 mm (or −10 mm) and b2=+60 mm e.g. for magnifying the beam cross section by the factor 6 (6-fold). The second telescope arrangement $T_2$ having cylindrical lens elements 25a, 25b expands the illumination radiation 3 parallel to the plane of incidence of the strip-shaped illumination beam 7 on the tape 8, for example by a factor of 14.3 (b1=+10 mm or −10 mm, b2=143 mm). The third telescope arrangement $T_3$ likewise having two cylindrical lens elements 26a, 26b expands the illumination beam 3 perpendicularly to the plane of incidence (in the Y-direction) for example by a factor of 50 (b1=+10 mm or b1=−10 mm, b2=500 mm).

In the case of the expansion unit 4a in FIG. 4, therefore, firstly illumination radiation 3 having a circular beam cross section having a diameter of 1 mm is converted to a circular beam cross section having a diameter of 6 mm, then to an oval beam cross section having a length of 86 mm and a width of 6 mm, and subsequently to an oval having a width of 86 mm and a length of 300 mm.

In order to optimize the smallest detectable particle size or the speed during the detection of particles for a respective application, it is advantageous to be able to alter the line width of the strip-shaped illumination beam 7 in the feed direction X. In order to perform such a variation in the examples of the expansion unit 4a shown in FIG. 3 and FIG. 4, it is advantageous if the focal length of at least one cylindrical lens element 22a, 22b of the first cylindrical lens element telescope $T_1$ in FIG. 3 or of a cylindrical lens element 24a, 24b of the second telescope $T_2$ in FIG. 4 is embodied as variable, e.g. by the provision of lens elements that can be varied in terms of their geometry. In the exemplary embodiment shown in FIG. 4, resulting beam widths upon the variation of the focal length b2 of the second cylindrical lens element 25b of the second telescope arrangement $T_2$ are indicated in the table below (Table 1):

TABLE 1

| Focal lengths (mm) | | | | | | Resulting beam | |
| $T_1$ | | $T_2$ | | $T_3$ | | | |
| b1 | b2 | b1 | b2 | b1 | b2 | Width (mm) | Length (mm) |
| −10 | +60 | −10 | 13.5 | −10 | 500 | 8.1 | 300 |
| −10 | +60 | −10 | 19.3 | −10 | 500 | 11.6 | 300 |
| −10 | +60 | −10 | 45.2 | −10 | 500 | 27.1 | 300 |
| −10 | +60 | −10 | 68.3 | −10 | 500 | 41.0 | 300 |
| −10 | +60 | −10 | 142.7 | −10 | 500 | 85.6 | 300 |

As has already been described further above, the expansion unit 4a is followed by the focusing unit 4b, which is designed as a cylindrical lens element which focuses the illumination radiation 3 or the illumination beam 7 on the tape 8, the beam cross section being reduced in the feed direction X. The focusing unit 4b in the form of a cylindrical lens element can have a focal length of 100 mm, for example, wherein the tape 8 should be situated as near as possible to the focal line of the focusing unit 4b. The variation of the beam cross section via a focusing unit 4b in the form of a cylindrical lens element can be gathered from the following table (Table 2) for different widths of the incident illumination radiation 3:

TABLE 2

| Incoming beam | | Resulting beam | |
|---|---|---|---|
| Width (mm) | Length (mm) | Width (μm) | Length (mm) |
| 8.1 | 300 | 10 | 300 |
| 11.6 | 300 | 7 | 300 |
| 27.1 | 300 | 3 | 300 |
| 41.0 | 300 | 2 | 300 |
| 85.6 | 300 | 1 | 300 |

As can be gathered from Table 2, in the present example the focusing leads to a reduction of the width of the beam cross section on the tape 8 by approximately a factor of 500, wherein factors of up to approximately 90 000 can also be used. For the stray light measurement, the linear illumination beam should not exceed a line width of approximately 10 μm to approximately 20 μm, wherein significantly smaller line widths (of less than 1 μm or 0.1 μm) are required for detecting particles in the sub-micrometers range.

It goes without saying that for illuminating tapes 8 having a large width B, it is also possible to use a plurality of beam shaping units 4 in a parallel manner, i.e. alongside one another in the Y-direction, such that larger resulting beam lengths arise. Via a five-fold parallelization, for example, from a beam length of 300 mm as illustrated in FIG. 2 to FIG. 4, it is possible to generate a beam length of 1500 mm in the Y-direction.

The illumination radiation S scattered into a solid angle range at the tape 8 or at the particles 10 situated in the region of the linear illumination is collimated at a collimation device 14 in the form of a further cylindrical lens element. In this case, the focal length of the collimation device 14 or of the cylindrical lens element typically corresponds to the distance from the tape 8, for example 100 mm. It goes without saying that the collimation device 14 can also have a plurality of cylindrical lens elements, e.g. along a line running in the Y-direction, in order to be able to collimate scattered illumination radiation S even in the case of tapes 8 having a large width B (of the order of magnitude of meters).

Accordingly, the detector unit 5 has one or a plurality of CCD linear detectors (1-dimensional detection) or CCD arrays (2-dimensional detection) arranged along a row (in the Y-direction). Optical waveguides (not shown) can be disposed upstream of the detectors, the optical waveguides being arranged in a linear fashion or in a 2-dimensional grid and serving for collecting the scattered illumination radiation S.

In addition or as an alternative to determining the degree of contamination or the particle density on the surface 8a of the tape 8, it may also be advantageous to obtain information about the thickness of the tape 8 or about the thickness of individual layers of the tape 8 during the processing of the tape 8.

Figure 5:
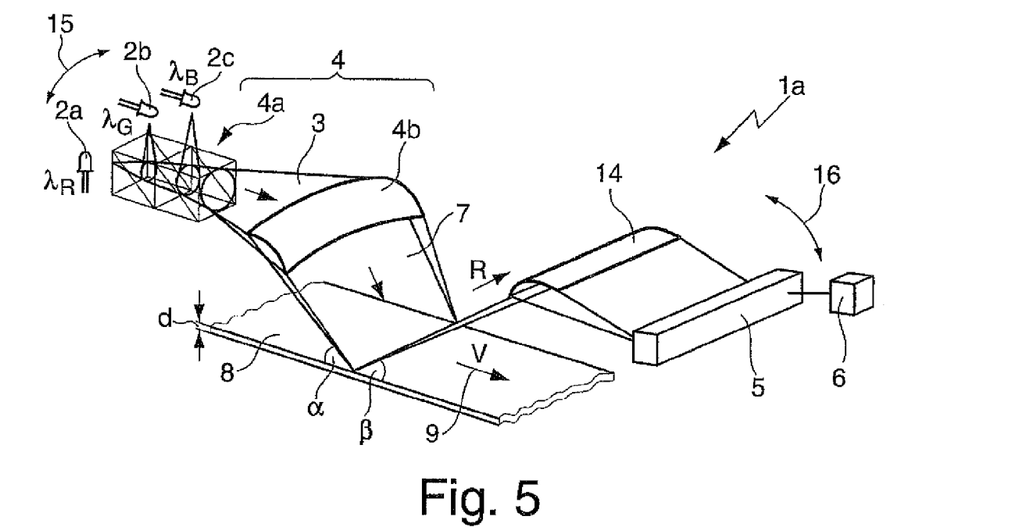
FIG. 5 shows a schematic illustration of an apparatus which, for determining layer thicknesses on a tape, performs a measurement of illumination radiation reflected at the tape.

FIG. 5 shows an apparatus 1a for determining the thickness D of layers of a film-like tape 8. The apparatus 1a in FIG. 5, like the apparatus 1 in FIG. 1, comprises a light generating unit, which consists of three light sources 2a to 2c in the present example. The light sources 2a to 2c are designed as laser diodes which generate illumination radiation 3 having a wavelength $\lambda_R$, $\lambda_G$, $\lambda_B$ in the red, green and blue wavelength range, i.e. at approximately 610 nm, 550 nm and 450 nm, respectively. The illumination radiation 3 is superimposed in a beam shaping unit 4, to put it more precisely in an expansion unit 4a, and, after focusing in a focusing unit 4b designed as a concave mirror, is converted into a strip-shaped illumination beam 7 having three wavelengths $\lambda_R$, $\lambda_G$, $\lambda_B$, which generates a linear illumination on the tape 8.

Illumination radiation R reflected from the tape 8 is collimated or focused via a concave mirror serving as collimation device 14 onto a linear detector 5 (strip-shaped detection). In order to measure the illumination radiation R specularly reflected at the tape 8, the angle $\alpha$ of incidence of the linear illumination beam 3 and the detection angle $\beta$ coincide ($\alpha=\beta$). An evaluation unit 6 connected to the detector 5 serves for determining the thickness d of a layer of the tape 8, which has a layer structure in the present example. If appropriate, it is also possible to determine the thicknesses of a plurality of layers or the total thickness of the tape.

In order to determine the layer thickness d, the intensity of the reflected illumination radiation R or the reflectivity of the tape 8 for the illumination radiation 3 is compared with known thickness-dependent reflectivity curves for a tape 8 having an identical layer structure. For the example of a tape 8 comprising a thin PMMA layer on a thin aluminum layer, FIG. 7b illustrates three reflectivity curves (R, G, B) for the reflectivity R (in %) at the respective three wavelengths $\lambda_R$, $\lambda_G$, $\lambda_B$ and an angle of incidence of $\alpha=90°$ (i.e. normal incidence) as a function of the layer thickness d of the PMMA layer (between 80 nm and 200 nm).

Figure 7A:
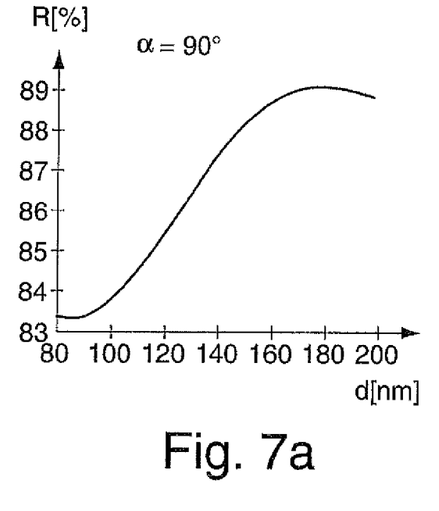
FIGS. 7a-d show graphs of the proportion of illumination radiation reflected at the tape as a function of the layer thickness of the tape.

FIG. 7a shows, by contrast, the reflectivity R (in %) of the tape 8 with the use of a broadband light source having a white light spectrum (of approximately 400 nm to approximately 800 nm), likewise for normal incidence ($\alpha=90°$). FIG. 7c shows a corresponding illustration for an angle of incidence of $\alpha=60°$. It is evident with reference to FIG. 7a,c that, for layer thicknesses of between approximately 100 nm and approximately 160 nm, the reflectivity changes substantially linearly, to be precise by approximately 5%, such that the thickness d in this thickness range can be determined with good accuracy. If the detector 5 has an intensity resolution of approximately 0.1%, thickness fluctuations of approximately 1.1 nm can be resolved in this case.

Figure 7B:
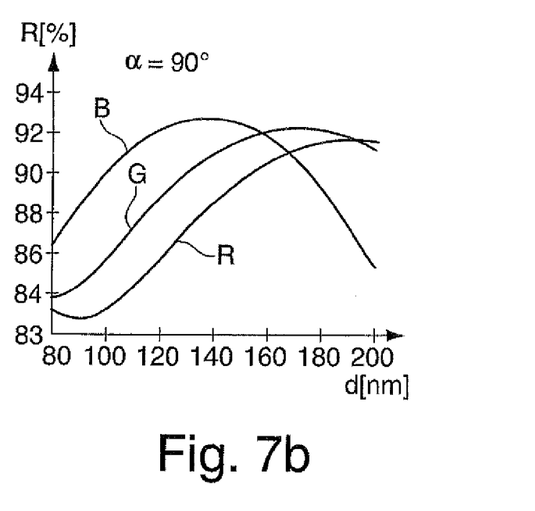
Figure 7C:
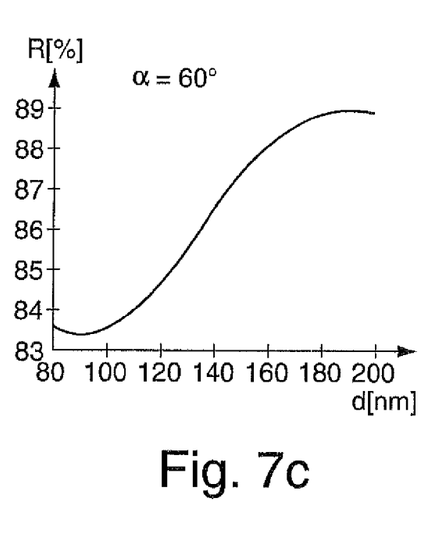

As is evident with reference to FIG. 7b, the thickness range in which significant variations of the reflectivity R occur is dependent on the wavelength chosen. It is therefore advantageous to choose illumination radiation having a wavelength which, in the thickness range to be detected, has a substantially linear profile of the reflectivity curve or the largest possible change in the reflectivity. It is particularly advantageous to perform a simultaneous measurement at a plurality of wavelengths (e.g. in the red, green and blue spectral range) in order to obtain the largest possible range in which the thickness measurement can be carried out, and in order to increase the measurement accuracy. In this case, it proves to be advantageous if the detector 5 contains selective receiver elements (sensor pixels) for three different wavelengths (e.g. of 450 nm, 550 nm and 610 nm), the receiver elements decomposing a white light spectrum, for example, into three colors, such that fast RGB spectrometry can be carried out.

Figure 6:
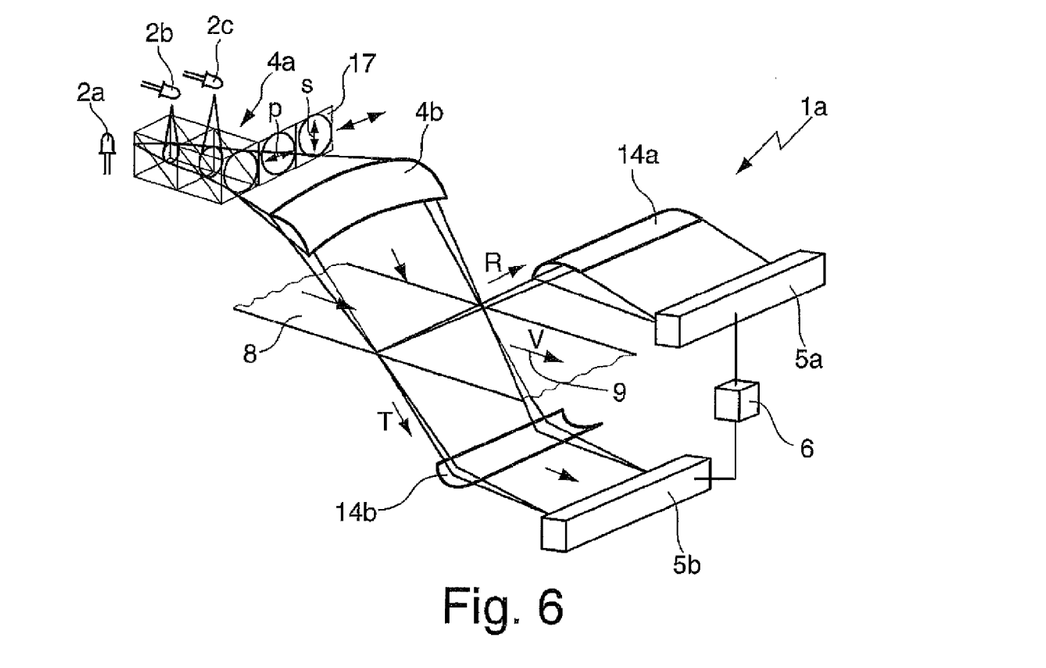
FIG. 6 shows an apparatus in which illumination radiation transmitted at the tape is additionally detected.
Figure 7D:
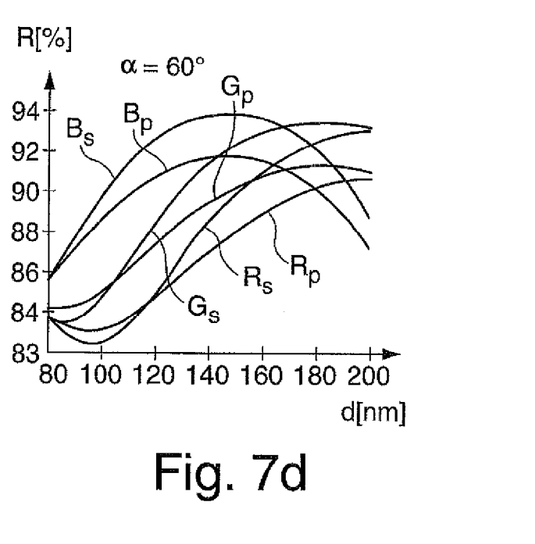

A further improvement with regard to the measurement range and the measurement accuracy is made possible if the illumination radiation is additionally separated into illumination radiation 3 polarized perpendicularly and parallel to the plane of incidence (ellipsometry). For this purpose, a modification of the apparatus 1a, as shown in FIG. 6, comprises a polarization filter 17, which can be introduced into the beam path of the illumination radiation 3 via a displacement device (not designated more specifically) and which allows optionally only s-polarized illumination radiation or only p-polarized illumination radiation to pass through, wherein the switching should take place synchronously with the line clock during the read-out of the detector 5. During the synchronous read-out of the line signals of the detector 5, six signals $R_s$, $G_s$, $B_s$, $R_p$, $G_p$, $B_p$ are thus obtained, which can be compared with thickness-dependent reflectivity curves, illustrated in FIG. 7d, in order to determine the thickness d of the layer composed of PMMA.

It goes without saying that the angle $\alpha$ of incidence and the detection angle $\beta$ can be adjusted depending on the respective application, i.e. the layer structure respectively to be examined or the respective layer material, for example by the light sources 2a to 2c being pivoted together with the beam shaping unit 4 via a pivoting unit 15 or by the collimation unit 14 being pivoted together with the detector 5 via a corresponding pivoting unit 16.

Moreover, in addition or as an alternative to the detection of the illumination radiation R reflected at the tape 8, the illumination radiation T transmitted at the tape 8 can also be measured. An apparatus 1a wherein both the reflected and the transmitted illumination radiation R, T are detected via a respective linear or matrix-type detector 5a, 5b is likewise illustrated in FIG. 6.

In the manner described in association with FIG. 5 and FIG. 6, it is possible to perform a fast and highly precise layer thickness measurement on tapes or on thin films. It goes without saying that in this case, in contrast to the illustration shown in FIG. 5 and FIG. 6, a refractive beam shaping unit 4 and/or collimation unit 14 can be used (or refractive and reflective optical units can be used in combination). As has already been illustrated further above in association with FIG. 1, the detector 5 used can be a continuous linear sensor extending over the entire width B of the tape 8 (e.g. having >20 000 pixels) or alternatively a plurality of linear sensors, the detection regions of which marginally adjoin one another or, if appropriate, marginally overlap one another.

Moreover, both the layer thickness measurement described in association with FIG. 5 and FIG. 6 and the determination of the degree of contamination or the particle density on the surface 8a of the tape 8 can be carried out on one and the same apparatus 1, 1a. For this purpose, it is necessary to vary the detection angle β and/or the angle α of incidence such that optionally reflected and/or scattered illumination radiation R, S are/is detected via the detector 5. In particular, the apparatus 1a for the stray light measurement as shown in FIG. 5 can be supplemented by one or a plurality of reference detectors 12, if they are not already present anyway in the apparatus 1a. Moreover, it is possible, of course, to use the apparatus from FIG. 1 for thickness measurement by suitably choosing the detection angle β and the angle α of incidence. In particular, it has proved to be advantageous here to design the beam shaping unit 4 such that the line width of the linear illumination on the tape 8 is variable, in order to be able to change over between the comparatively small line width of approximately 1 μm for the stray light measurement and the comparatively large line width for the thickness measurement in the range around approximately 100 μm.

The invention claimed is:

1. An apparatus, comprising:
a light generating unit configured to generate illumination radiation;
a beam shaping unit downstream of the light generating unit along a path of the illumination radiation, the beam shaping unit comprising an optical element having an adjustable focal length so that the beam shaping unit is configured to shape a strip-shaped illumination beam to linearly illuminate with a variable line width a surface of a tape transversely with respect to a feed direction of the tape;
a detector unit configured to detect illumination radiation scattered, reflected and/or transmitted by the tape;
an evaluation device configured to determine a degree of contamination of the surface of the tape on a plurality of tape sections based on the detected illumination radiation, each tape section extending in the feed direction of the tape; and
a polarization filter device configured to set a polarization of the illumination radiation to generate linearly polarized illumination radiation having a direction of polarization that is switchable between two mutually orthogonal polarization states,
wherein the apparatus is configured so that an angle between the tape and the detector unit to detect the illumination radiation scattered, reflected and/or transmitted by the tape is adjustable.

2. The apparatus of claim 1, wherein the illumination radiation has a wavelength range of between 300 nm and 1000 nm.

3. The apparatus of claim 1, wherein the illumination radiation comprises three different spectral ranges.

4. The apparatus of claim 3, wherein a first spectral range is in a red color spectral range, a second spectral range is a blue color range, and a third spectral range is a green color spectral ranges.

5. The apparatus of claim 1, wherein the light generating device comprises first and second light sources, the first light source is configured to generate illumination light in a first spectral range, and the second light source is configured to generate light in a second spectral range which is different from the first spectral range.

6. The apparatus of claim 1, wherein the detector device comprises a spectrally resolving detector configured to simultaneously detect two different wavelengths of the illumination radiation.

7. The apparatus of claim 1, wherein the detector device comprises a spatially resolving detector configured to spatially resolve detection of the illumination radiation in a direction transverse to the feed direction.

8. The apparatus of claim 1, wherein the apparatus is configured so that an angle of incidence of the illumination beam on the surface of the tape is adjustable.

9. The apparatus of claim 1, wherein the movement unit is configured to move the tape at a velocity of at least one meter per minute.

10. The apparatus of claim 1, wherein the beam shaping unit comprises a telescope arrangement configured to expand the beam of the illumination radiation in the feed direction.

11. The apparatus of claim 1, wherein the evaluation device is configured to detect exceeding a limit value of a degree of contamination of the surface of the tape and/or of a limit value of a change in a degree of contamination of the surface of the tape.

12. The apparatus of claim 1, further comprising a reference detector configured to determine an intensity of the illumination radiation.

13. The apparatus of claim 1, wherein the optical element comprises a lens.

14. The apparatus of claim 1, wherein the optical element comprises a cylindrical lens.

15. The apparatus of claim 1, wherein the optical element comprises a zoom lens.

16. The apparatus of claim 1, wherein the optical element comprises a mirror having a shape that is variable to adjust the focal length.

17. An apparatus, comprising:
a light generating unit configured to generate illumination radiation;
a beam shaping unit downstream of the light generating unit along a path of the illumination radiation, the beam shaping unit comprising an optical element having an adjustable focal length so that the beam shaping unit is configured to shape a strip-shaped illumination beam to linearly illuminate with a variable line width a surface of a tape transversely with respect to a feed direction of the tape;
a detector unit configured to detect illumination radiation scattered, reflected and/or transmitted by the tape;
an evaluation device configured to determine a degree of contamination of the surface of the tape on a plurality of tape sections based on the detected illumination radiation, each tape section extending in the feed direction of the tape; and
a polarization filter device configured to set a polarization of the illumination radiation to generate linearly polarized illumination radiation having a direction of polarization that is switchable between two mutually orthogonal polarization states,
wherein:
the light generating device comprises first and second light sources;
the first light source is configured to generate illumination light in a first spectral range;

the second light source is configured to generate light in a second spectral range which is different from the first spectral range;

the detector device comprises a spectrally resolving detector configured to simultaneously detect the illumination light in the first and second spectral ranges, and the apparatus is configured so that an angle of incidence of the illumination beam on the surface of the tape is adjustable.

18. The apparatus of claim 17, wherein the apparatus is configured so that an angle between the tape and the detector unit to detect the illumination radiation reflected, transmitted and/or scattered at the tape is adjustable.

19. The apparatus of claim 17, wherein the spatially resolving detector is configured to spatially resolve detection of the illumination radiation in a direction transverse to the feed direction.

20. An apparatus, comprising:
- a light generating unit configured to generate illumination radiation;
- a beam shaping unit downstream of the light generating unit along a path of the illumination radiation, the beam shaping unit comprising an optical element having an adjustable focal length so that the beam shaping unit is configured to shape a strip-shaped illumination beam to linearly illuminate with a variable line width a surface of a tape transversely with respect to a feed direction of the tape;
- a detector unit configured to detect illumination radiation scattered, reflected and/or transmitted by the tape;
- an evaluation device configured to determine: a degree of contamination of the surface of the tape on a plurality of sections of the tape based on the detected illumination radiation, each tape section extending in the feed direction of the tape; and
- a polarization filter device configured to set a polarization of the illumination radiation to generate linearly polarized illumination radiation having a direction of polarization that is switchable between two mutually orthogonal polarization states, wherein:
the apparatus is configured so that an angle of incidence of the illumination beam on the surface of the tape is adjustable; and the apparatus is configured so that an angle between the tape and the detector unit to detect the illumination radiation reflected, transmitted and/or scattered at the tape is adjustable.

* * * * *

UNITED STATES PATENT AND TRADEMARK OFFICE
CERTIFICATE OF CORRECTION

PATENT NO. : 9,250,062 B2
APPLICATION NO. : 14/196757
DATED : February 2, 2016
INVENTOR(S) : Bernd Doerband and Ralf Lindner

It is certified that error appears in the above-identified patent and that said Letters Patent is hereby corrected as shown below:

In the Specification

Col. 2, line 20, after "cleaning", insert -- . --.

Col. 14, line 3, delete "FIG." and insert -- FIGS. --.

Signed and Sealed this
Fourteenth Day of June, 2016

Michelle K. Lee
*Director of the United States Patent and Trademark Office*